United States Patent
Strohm

(10) Patent No.: US 11,224,531 B2
(45) Date of Patent: Jan. 18, 2022

(54) HIGH-PRECISION ADJUSTABILITY WEIGHT-LIFTING BELT

(71) Applicants: General Leathercraft Manufacturing, Inc., Coleman, TX (US); Steven Strohm, Forest Hills, NY (US)

(72) Inventor: Steven Strohm, Forest Hills, NY (US)

(73) Assignee: General Leathercraft Manufacturing, Inc., Coleman, TX (US)

( * ) Notice: Subject to any disclaimer, the term of this patent is extended or adjusted under 35 U.S.C. 154(b) by 274 days.

(21) Appl. No.: 16/406,113

(22) Filed: May 8, 2019

(65) Prior Publication Data

US 2019/0343674 A1  Nov. 14, 2019

Related U.S. Application Data

(60) Provisional application No. 62/668,861, filed on May 9, 2018.

(51) Int. Cl.
*A61F 5/02* (2006.01)
*A41F 9/02* (2006.01)
*A41F 9/00* (2006.01)

(52) U.S. Cl.
CPC .............. *A61F 5/028* (2013.01); *A41F 9/002* (2013.01); *A41F 9/025* (2013.01)

(58) Field of Classification Search
CPC ........... A41F 9/002; A41F 9/025; A61F 5/028
See application file for complete search history.

(56) References Cited

U.S. PATENT DOCUMENTS

| | | | | |
|---|---|---|---|---|
| 603,760 A | * | 5/1898 | Gair | A41F 9/002 2/322 |
| 1,095,947 A | * | 5/1914 | Thorp | A41F 9/002 2/338 |
| 1,100,389 A | * | 6/1914 | Miller | A41F 9/002 24/182 |
| 1,851,106 A | * | 3/1932 | Mix | A41F 9/002 2/339 |
| 1,894,654 A | * | 1/1933 | Wirth | A44B 11/24 24/178 |
| 2,137,796 A | * | 11/1938 | Bayliss | A41F 9/002 2/322 |
| 2,194,734 A | * | 3/1940 | Brenner | A41F 9/002 2/320 |
| 3,171,409 A | * | 3/1965 | Cetrone | A61F 5/028 128/99.1 |
| 3,566,454 A | * | 3/1971 | Schmidt | A44B 11/28 24/165 |

(Continued)

*Primary Examiner* — Shaun R Hurley
*Assistant Examiner* — Bao-Thieu L Nguyen
(74) *Attorney, Agent, or Firm* — William P. O'Sullivan

(57) ABSTRACT

A belt is disclosed that includes a strap and a buckle. A first row of holes extends in a longitudinal direction, and a second parallel row of holes extends in the longitudinal direction, both near a first end of the strap. The holes in the first row are offset in the longitudinal direction from the holes in the second row. The belt buckle has a frame and a prong and is coupled to the second end of the strap. The buckle is configured such that when the first end of the belt is passed through the frame of the buckle, the prong of the buckle can be moved into either a first position to physically engage a hole in the first row of holes or a second position to physically engage a hole in the second row of holes.

19 Claims, 3 Drawing Sheets

(56) References Cited

U.S. PATENT DOCUMENTS

| | | | | |
|---|---|---|---|---|
| 3,829,902 | A * | 8/1974 | Fisher | A41F 9/002 2/338 |
| 3,848,271 | A * | 11/1974 | Goele | A41F 9/002 2/338 |
| 4,470,174 | A * | 9/1984 | Rhea | A41F 9/002 24/16 PB |
| 4,545,370 | A * | 10/1985 | Welsh | A61F 5/028 128/95.1 |
| 4,802,667 | A * | 2/1989 | Altner | A61F 5/028 2/338 |
| 5,054,433 | A * | 10/1991 | Pfleger | A01K 27/005 119/856 |
| 5,226,195 | A * | 7/1993 | Pappas, Jr. | A41F 9/002 2/321 |
| 5,511,703 | A * | 4/1996 | Ryerson | B25H 3/00 224/682 |
| 6,530,128 | B2 * | 3/2003 | Bunjes | A44B 11/24 24/177 |
| 10,258,347 | B2 * | 4/2019 | Hopman | A61B 17/1322 |
| 2005/0217080 | A1 * | 10/2005 | Kojoori | A44C 5/14 24/265 WS |
| 2007/0094776 | A1 * | 5/2007 | Stevens | A44C 5/00 2/338 |
| 2011/0034845 | A1 * | 2/2011 | Polliack | A61F 5/0193 602/19 |
| 2013/0324898 | A1 * | 12/2013 | Polliack | A61F 5/0193 602/18 |
| 2015/0107002 | A1 * | 4/2015 | Wang | A41F 9/002 2/338 |
| 2017/0188665 | A1 * | 7/2017 | Greenham | A44B 11/008 |

* cited by examiner

HIGH-PRECISION ADJUSTABILITY WEIGHT-LIFTING BELT

CROSS REFERENCE TO RELATED APPLICATION

This application claims the benefit of U.S. Patent Application Ser. No. 62/668,861, filed May 9, 2018, entitled "HIGH-PRECISION ADJUSTABILITY WEIGHT-LIFTING BELT," which is hereby incorporated by reference herein in its entirety.

FIELD OF THE INVENTION

This disclosure relates to a belt and, more particularly, relates to a belt (e.g., for weight-lifting) that has a high degree of structural integrity, yet allows for highly precise adjustability in wearable length.

BACKGROUND

Belts are used for a variety of reasons. One type of belt (i.e., a weight-lifting belt) may help weight lifters avoid lower back and other injuries.

SUMMARY OF THE INVENTION

In one aspect, a belt is disclosed that includes a strap and a buckle. The strap has a first end and a second end opposite the first end. A first row of holes extends in a longitudinal direction near the first end of the strap, and a second row of holes extends in the longitudinal direction near the first end of the strap. The second row is parallel to the first row. The holes in the first row are offset in the longitudinal direction from the holes in the second row. In a typical implementation, this offset ensures that no two holes provide the same degree of belt tightness when physically engaged to the belt buckle. The belt buckle has a frame and a prong and is coupled to the second end of the strap. The buckle is configured such that when the first end of the belt is passed through the frame of the buckle, the prong of the buckle can be moved into either a first position to physically engage a hole in the first row of holes or a second position to physically engage a hole in the second row of holes.

In another aspect, a method of wearing (and adjusting) this sort of belt is disclosed. More particularly, the method includes wrapping the belt around a person's waist; passing the first end of the strap through the frame of the buckle; tightening the belt to a desired tightness; selecting a first hole for the prong between the first row of holes and the second row of holes; pivoting the prong laterally, or sliding the prong along an end bar to align with the first selected hole; and passing the prong through the first selected hole to rest against an anchor bar of the frame of the buckle.

In some implementations, the method further includes: pulling at the strap to disengage the prong from the selected hole; loosening or tightening the belt as desired; selecting a second hole for the prong, where the second hole is in a different one of the rows than the first selected hole; pivoting the prong laterally, or sliding the prong along the end bar to align with the second selected hole; and passing the prong through the second selected hole to rest against the anchor bar of the frame of the buckle.

In some implementations, one or more of the following advantages are present.

For example, the hole-spacing and prong movement can be applied to weightlifting belts and pants belts for a vastly improved fit. It is especially important in the lifting of weights because a belt that is too tight or too loose can be dangerous for back/spinal health. The tighter effective hole-spacing allows for the wearer to adjust based on day to day weight fluctuations, for example, as opposed to being "in between" holes on certain days. With this combination of slidable (or pivotable) prong and offset holes, the size increments can be as small as a quarter of an inch (or smaller). And this can be achieved without compromising the structural integrity or strength (especially hole-to-hole) of the belt.

Other features and advantages will be apparent from the description and drawings, and from the claims.

BRIEF DESCRIPTION OF THE DRAWINGS

Like reference characters refer to like elements.

DETAILED DESCRIPTION

Figure 1:
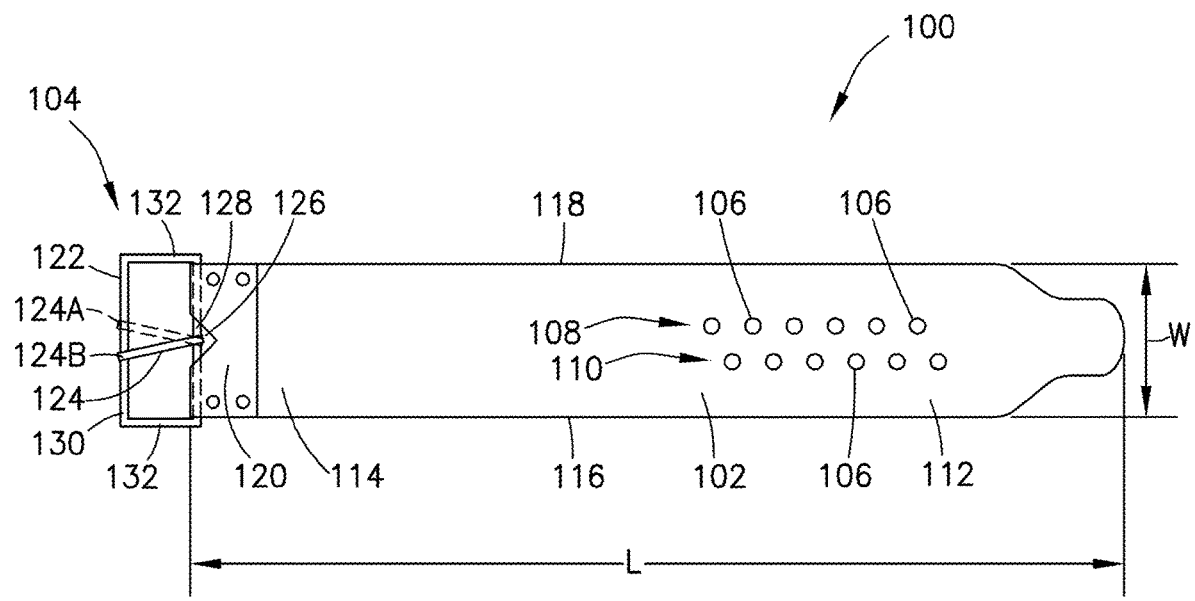
FIG. 1 is front view showing an exemplary implementation of a belt (e.g., a weight lifting belt) that has a strap and a buckle.

FIG. 1 is front view showing an exemplary implementation of a belt 100 that has a strap 102 and a buckle 104. The belt 100 can be any kind of belt, but in some implementations, is a weight lighting belt. A weight lifting belt is typically wide and thick. For example, in some implementations, the strap 102 of the belt 100 may have a thickness between 9 millimeters and 15 millimeters (or between 3 millimeters and 15 millimeters), and at least a portion of the strap 102 (or the entire strap) may have a width that is between 30 millimeters and 125 millimeters. It can be made of a variety of materials including, for example, leather.

Wearing a weight lifting belt can provide a variety of benefits, particularly to those seeking to lift heavy weights. It is important, of course, that the weight lifting belt fit correctly. A limiting factor in achieving a good fit for some traditional weight lifting belts is the fact that the spacing between holes in the belt (that the buckle engages) needs to be sufficiently large to ensure adequate structural integrity of the belt. One way to make the adjustability of belt length more precise would be to move the holes on the belt closer together. Experience tells us, however, that, at some point, moving the holes on a belt closer together compromises the structural integrity of the belt between the holes, which can be a particularly problematic if the belt is under a heavy load, which weight lifting belts often are.

The illustrated belt 100 solves this problem by providing a staggered arrangement of holes 106 in the strap 102 of the belt 100 and a buckle 104 that is configured to engage any one of the staggered holes. More particularly, in the illustrated implementation, the staggered pattern of holes 106 forms two rows 108, 110 of holes 106 and the buckle 104 has a prong 124 that can swing back and forth (as indicated by arrow A) between a first position (124A) to line up with (and, therefore, possibly engage) any one of the holes 106 in row 108, or a second position (124B) to line up with a hole in row 110.

In a typical implementation, the distance between adjacent holes 106 in each respective row 108 or 110 is sufficient to provide structural integrity to the strap 102 (from hole-to-hole in a single row), even under heavy loads, and the staggered nature of the holes 106 provides a greater degree of precision in adjustability of belt length around the wearer. In a typical implementation, the distance between adjacent holes 106 in a single row (108 or 110) will depend, in part on the material and thickness of the strap 102, but, in a typical implementation, that distance is no smaller than 1 inch. The distance between adjacent holes 106 in a single row may be larger than that, of course, but making that distance as small as practical can help maximize the precision in adjustability of the belt length around the wearer.

The illustrated strap 102 is an elongated piece of flat, flexible material (e.g., leather). The strap 102 has a length L, a width W, and a thickness T (into the page). The strap 102 has a first end 112 and a second end 114 that is opposite the first end 112. The staggered holes 106 extend completely through the strap 102 and the rows 108, 110 of holes are near the first end 112 of the strap 102. The holes 106 in the first row 108 extend along a first imaginary line (that runs in a lengthwise direction, parallel to the major side edges 116, 118 of the strap 102) near the first end 112 of the strap 102. The holes 106 in the second row 110 of holes extend along a second imaginary line (that also runs in the lengthwise direction, parallel to the major side surfaces of the strap 102 and parallel to the first imaginary line). Each hole 106 in the first row 108, for example, is offset in the longitudinal direction from a corresponding hole 106 in the second row 110. The shortest distance, along a surface of the strap 102, between a hole and the buckle-end (e.g., at 120) of the strap 102, is different for every hole 106.

The buckle 104, in the illustrated implementation, has a frame 122 and one, and only one, prong 124. Moreover, the illustrated buckle 104 is configured such that when the first end 112 of the strap 102 is passed through the frame 122 of the buckle 104, the prong 124 of the buckle 104 can laterally pivot (e.g., be moved into either a first position to line up with the first row 108 of holes or a second position to line up with the second row 110 of holes. The overall belt configuration (i.e., the prong 124, the frame 122, and the strap) facilitates this capability of the prong 124 to laterally pivot. For example, in the illustrated implementation, the prong 124 is loosely coupled to the frame 122 so that the prong 124 can wiggle a bit (to align with the first 108 or second 110 row of holes 106) relative to the frame 122, and a notch 126 is formed where the prong extends through the strap 102 material and the notch 126 is sized to allow the indicated wiggling.

The frame 122 of the buckle 104 can, of course, take on a variety of different shapes, sizes, and styles. In the illustrated implementation, the frame 122 is rectangular, with four sides, including: an end bar 128 at a first end of the frame (where the strap 102 is attached), an anchor bar 130 at a second end of the frame (opposite the end bar 128), and two side bars 132, attaching the end bar 128 to the anchor bar 130.

A distal portion of strap 102 (at the second end 114 of the strap 102) is wrapped around a portion of the end bar 128 of the buckle 104 and secured to itself. In this regard, the wrapped-around portion of the strap 102 can be secured in any number of possible ways (with adhesive, rivets, etc.). In the illustrated example, the wrapped-around portion of the strap 102 is secured with four rivets. The notch 126, through which the prong 124 extends, is formed in the wrapped-around portion of the strap 102.

As mentioned above, the prong 124 is able to laterally pivot (e.g., swing back and forth between a first position 124A and a second position 124B, as indicated by arrow A). The prong 124, of course, is able to swing about an axis defined by the end bar 128 of the frame 122 of the buckle 104, too.

There are a number of ways that the prong 124 might physically engage the end bar 128. In the illustrated example, the prong has a first, proximate end that defines a circular opening (not visible in FIG. 1), through which the end bar 128 passes, and a second, distal end that can be positioned to pass through one of the holes in the first row of holes or the second row of holes and rest against the anchor bar 130 of the frame. In a typical implementation, the prong 124 is long enough that it can physically rest against the anchor bar 130 regardless of whether the prong 124 is in the first position (to align with the first row 108 of holes), the second position (to align with the second row 110 of hoes), or anywhere in between.

Figure 2:
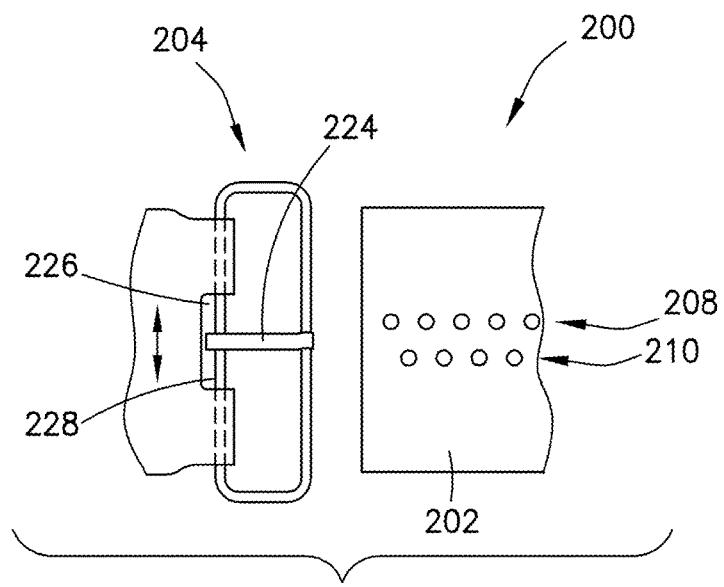
FIG. 2 is a partial front view showing another exemplary implementation of a belt (e.g., a weight lifting belt) that has a strap and a buckle.

FIG. 2 is a partial front view showing another exemplary implementation of a belt 200 that has a strap 202 and a buckle 204. The belt 200 in this implementation can be any kind of belt including, for example, a weight lighting belt.

The belt 200 in FIG. 2 is, in many ways, similar to the belt 100 in FIG. 1. The most notable difference between the belt 200 in FIG. 2 and the belt 100 in FIG. 1 is that the prong belt 200 in the belt 200 of FIG. 2 does not markedly laterally pivot (like the belt 100 in FIG. 1). Instead, the belt 200 in FIG. 2 slides laterally along the end bar 228 of the buckle 204 (as indicated by the arrow), between a first position (aligned with and, therefore, able to engage with the holes in a first row 208 of holes) and a second position (aligned with and, therefore, able to engage with the holes in a second row 208 of holes).

The first end of the prong 224, in the illustrated implementation, is coupled to the end bar 228 sufficiently loosely and the notch 226 in the strap 202 material is sufficiently large to allow the prong 224 to slide along the end bar 228.

Figure 3:
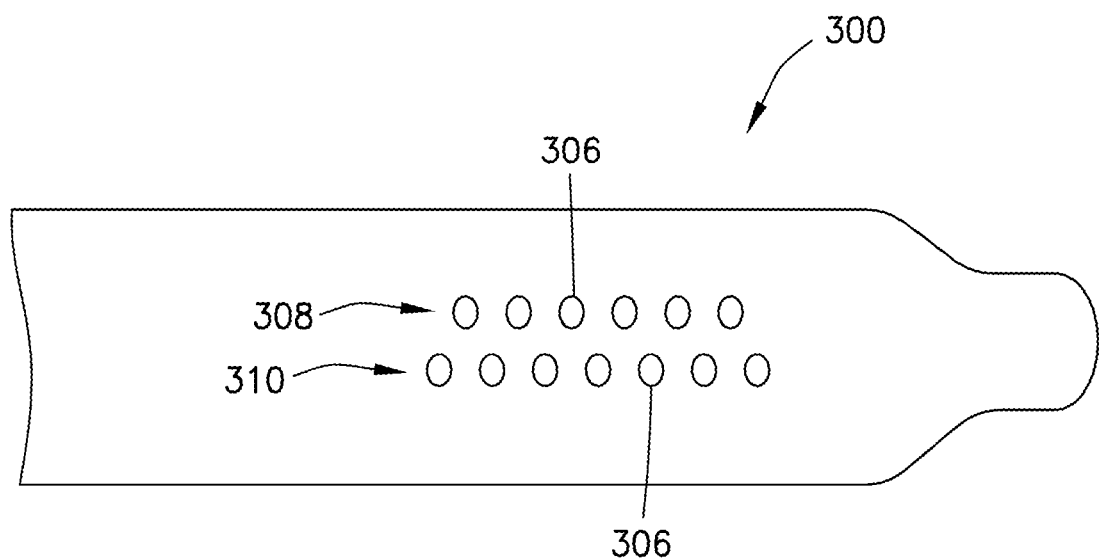
FIG. 3 is a partial front view showing one end of an exemplary belt (e.g., a weight lifting belt) that has holes arranged in a staggered pattern that includes two rows.

FIG. 3 is a partial front view showing one end of an exemplary belt 300 that has holes 306 arranged in a staggered pattern that includes two rows 308 and 310.

Figure 4:
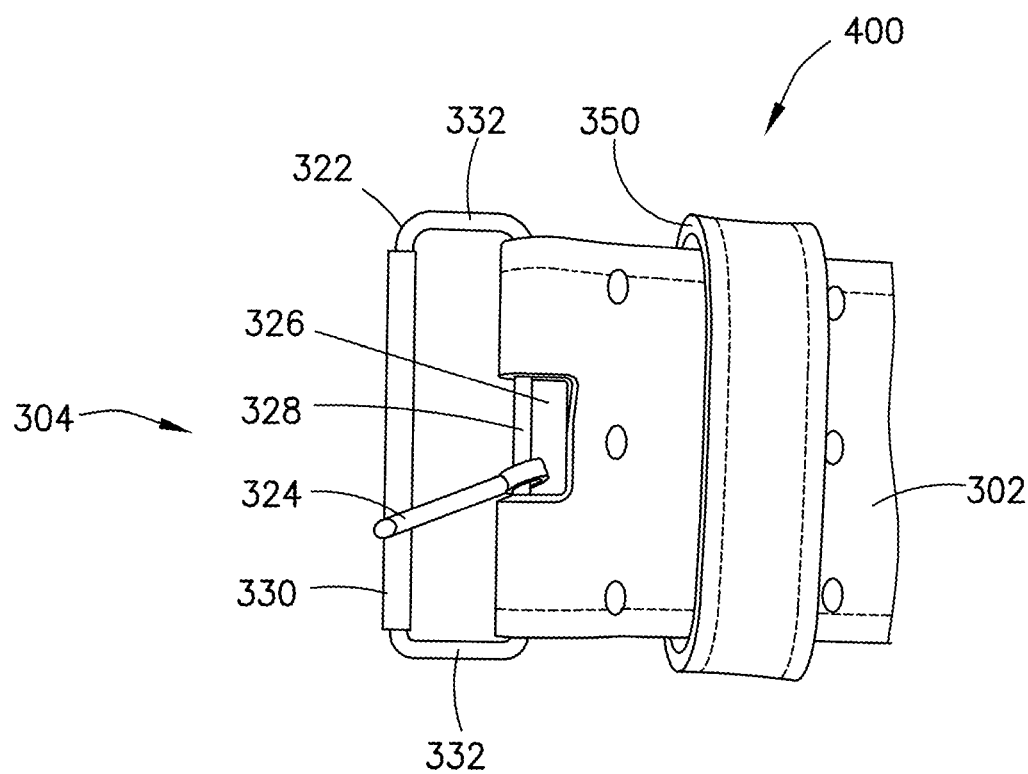
FIG. 4 is a partial front view showing the other end of the exemplary belt from FIG. 3.

FIG. 4 is a partial front view showing the other end of the exemplary belt 300 from FIG. 3. The belt 400 has a buckle 304 at that other end. The buckle has a frame 322 (with an end bar 328, anchor bar 330 and two side bars 332), and a prong 324. The prong 324, in the illustrated implementation, is able to both slide (laterally along the end bar 328) and pivot (laterally, from orthogonal to the end bar) to engage a hole from either of the two rows (308 or 310) of holes (see, FIG. 3). The notch 326 in the strap 302 material, through which the prong 324 extends, is rectangular in shape and allows both the sliding and pivoting of the prong 324. The illustrated belt 400 also has a loop 350, through which the non-buckle end of the belt can pass. The loop 350 is made from the same material as the strap 302 and is securely fastened to the strap 302. The strap 302 is wrapped around the end bar 328 of the buckle 304 and held in place with six rivets.

Figure 5:
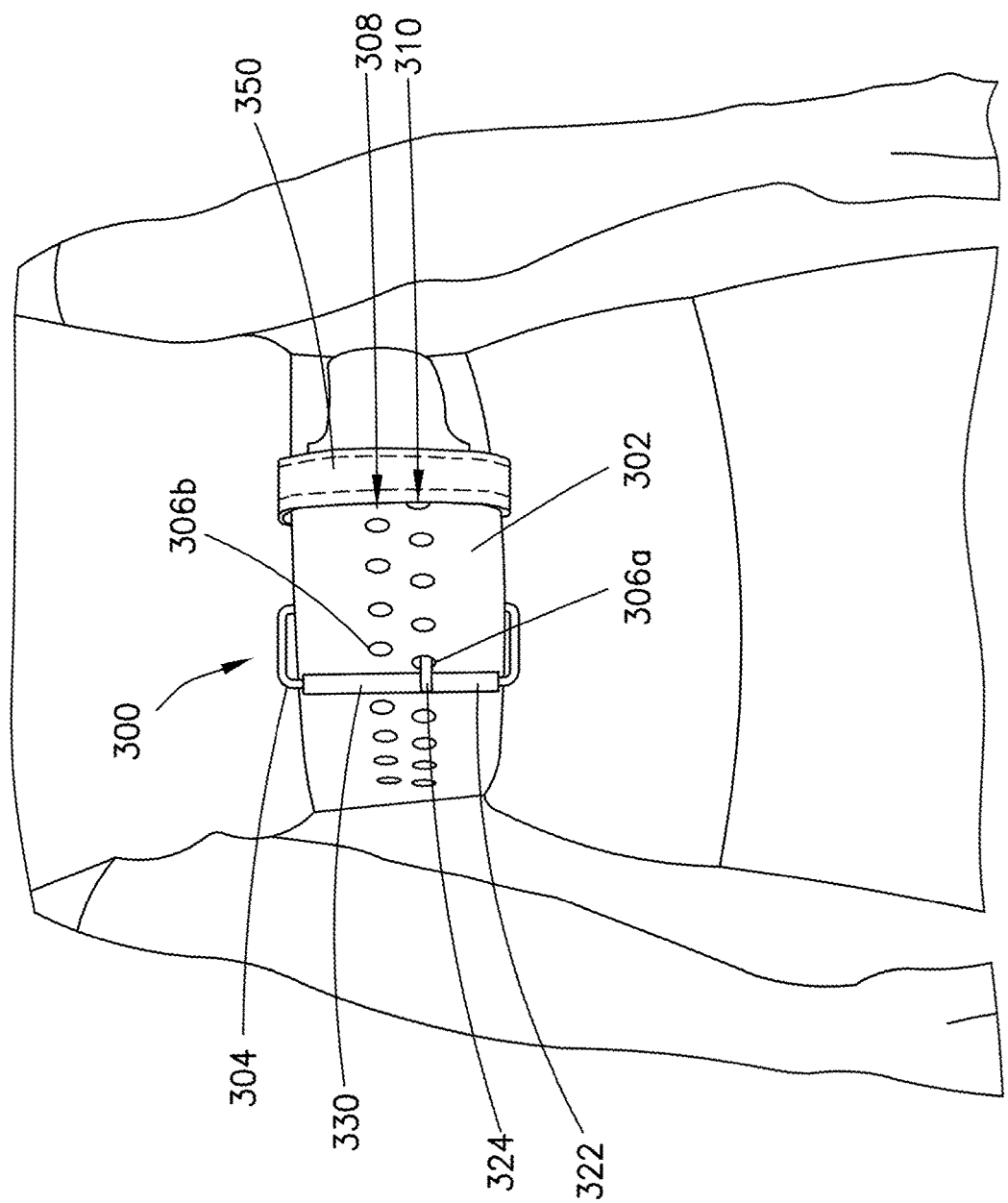
FIG. 5 is a front view of a person (e.g., a weight lifter) wearing a belt (e.g., a weight lifting belt).

A weight lifter, for example, can advantageously utilize the belt(s) disclosed herein to gain a great fit. In this regard, the weight lifter, for example, might wrap the belt 300 around his or her waist as shown, for example, in FIG. 5.

To do this, the weightlifter would pass the first end of the strap through the frame 322 of the buckle 304, tighten the belt 300 to a desired tightness, select a first hole 306 (in either the first row 308 or the second row 310) for the prong 324 to enter, pivot (or slide) the prong laterally, along or relative to the end bar (not shown) of the frame 322) to align with the first selected hole, and then pass the prong 324 through the first selected hole (306a, in the illustrated implementation) to rest against the anchor bar 330 of the frame 322 of the buckle 304. The weightlifter may pass the far end of the belt through the loop 350.

To further adjust the belt (e.g., if the belt in the selected position does not quite fit right), the weightlifter might pull at the strap 302 to disengage the prong 324 from the selected hole (306a), loosen or tighten the belt as desired; select a second hole for the prong (in some implementations where only a small adjustment is needed, for example, the second hole (306b) might be the closest hole in a different row than the first selected hole), pivot (or slide) the prong laterally (as required) to align with the second selected hole (306b), and pass the prong 324 through the second selected hole (306b) to rest against the anchor bar 330 of the frame of the buckle.

A number of embodiments of the invention have been described. Nevertheless, it will be understood that various modifications may be made without departing from the spirit and scope of the invention.

For example, the belt's strap can be made in a variety of different sizes and shapes. Each dimension of the belt's strap (e.g. length, thickness, width, etc.) can vary from belt to belt and even in different sections of a single belt. In an exemplary implementation, the strap has a thickness between 3 millimeters and 15 millimeters. In an exemplary implementation, at least a portion (or all) of the strap has a width that is between 30 millimeters and 125 millimeters. The length can be virtually any length (e.g., between 500 millimeters (or less) to 1300 millimeters (or more)). A variety of different materials (e.g., leather, fabric, etc.) and/or combinations of materials can be used to make the belt's strap.

The arrangement of holes can vary from what is specifically shown in the drawings. For example, in some implementations, there can be three (or more) parallel rows of holes, instead of just two. The offset between adjacent rows of holes can vary from what is disclosed herein. For example, in implementations that have two rows of holes, the offset can be such that a hole in one row is located in the middle of where two other holes from another row are located (as measured from an end of the belt). However, that need not be the case. Similarly, in implementations that have three rows of holes, the degree of offset between the holes in adjacent rows can be one third the distance between adjacent holes in a single row. However, that need not be the case either. In some implementations, the spacing between holes in a single row can be uniform. However, in some implementations, the spacing between holes in a single row varies. In some implementations, the holes may be arranged in approximate rows, without the rows being clearly defined. The spacing between adjacent rows of holes can be uniform or varying. In one exemplary implementation, the belt has two rows of holes that are offset by half the distance between each hole (in a single row). The holes can be formed in any number of possible ways, typically by punching. Typically, all of the holes have the ne diameter, though that need not be the case. Typically, the rows of holes are arranged centered and symmetrically on the strap (from top side to bottom side), though that need not be the case either. Each row can have the same number of holes as the other row(s), or a different number of holes as the other row(s).

The belt buckle can have any number of a variety of possible configurations. The frame of the belt buckle, for example, can be any size or shape (e.g., rectangular (as shown in some of the figures), D-shaped, square, round, oval, etc.) The prong, too, can have a variety of different shapes (curved, bent straight, etc.) and sizes (e.g., different thicknesses and/or lengths). Generally speaking, however, the frame is large enough so that the strap of the belt can pass through it and the prong is narrow enough to pass through the holes formed in the belt's strap. The belt buckle can be made from any one of a variety of different materials or combinations of material. Typically, the belt buckle is rigid (and may be made of metal, for example). The belt (e.g., the strap and/or the buckle) can include any number of a variety of different decorative elements or features.

Any relative terminology used herein, such as "upper", "lower", "above", "below", "front", "rear," etc. has been used solely for the purposes of clarity and is not intended to limit the scope of what is described here or to require particular positions or orientations. Accordingly, such relative terminology should not be construed to limit the scope of the present application.

Other implementations are within the scope of the claims.

What is claimed is:

1. A belt comprising:
   a strap having a first end and a second end opposite the first end;
   a first row of holes that extends in a longitudinal direction near the first end of the strap;
   a second row of holes that extends in the longitudinal direction near the first end of the strap,
   wherein the second row is parallel to the first row,
   wherein the holes in the first row are offset in the longitudinal direction from the holes in the second row; and
   a buckle coupled to the second end of the strap,
   wherein the buckle comprises a frame and a prong,
   wherein the frame comprises an end bar, to which the prong is physically coupled, and an anchor bar, against which the prong is able to rest,
   wherein the buckle is configured such that when the first end of the belt is passed through the frame of the buckle, at least a portion of the prong of the buckle is able to be moved relative to the frame of the buckle, between a first position where the prong extends through a hole in the first row of holes and rests against the anchor bar of the frame, and a second position where the prong extends through a hole in the second row of holes and rests against the anchor bar of the frame,
   wherein the holes in the first row of holes are staggered relative to the holes in the second row of holes, and
   wherein the first and second rows of holes are centered and symmetrical on the strap between a top side of the strap and bottom side of the strap.

2. The belt of claim 1, wherein the prong, the frame, and the strap are configured to enable the prong to be moved between at least the two different positions.

3. The belt of claim 1, wherein the frame comprises:
   an end bar at a first end of the frame; and
   an anchor bar at a second end of the frame that is opposite the first end of the frame,
   wherein the prong is physically attached to, and able to swing about, the end bar of the frame.

4. The belt of claim 3, wherein the prong comprises:
   a first end that defines a circular opening, through which the end bar passes; and a second end that can be positioned to pass through one of the holes in the first row of holes or the second row of holes and rest against the anchor bar of the frame.

5. The belt of claim 4, wherein a portion of strap at the first end of the belt is wrapped around the end bar of the frame, and wherein the prong extends through a notch in the wrapped-around portion of the strap.

6. The belt of claim 5, wherein the prong is able to laterally pivot, or slide along the end bar, between the first position and the second position.

7. The belt of claim 6, wherein the first end of the prong is coupled to the end bar sufficiently loosely and the notch is sufficiently large to allow the prong to laterally pivot, or slide along the end bar, between the first position and the second position.

8. The belt of claim 1, wherein the buckle has one and only one prong.

9. The belt of claim 1, wherein the strap has a thickness between 3 millimeters and 15 millimeters, and at least a portion of the strap has a width that is between 30 millimeters and 125 millimeters.

10. The belt of claim 1, wherein the belt is a weight lifting belt.

11. A method of wearing a belt, wherein the belt comprises:
a strap having a first end and a second end opposite the first end;
a first row of holes that extends in a longitudinal direction near the first end of the strap;
a second row of holes that extends in the longitudinal direction near the first end of the strap,
wherein the second row is parallel to the first row,
wherein the holes in the first row are offset in the longitudinal direction from the holes in the second row;
a buckle coupled to the second end of the strap,
wherein the buckle comprises a frame and a prong,
wherein the frame comprises an end bar, to which the prong is physically coupled, and an anchor bar, against which the prong is able to rest,
wherein the buckle is configured such that when the first end of the belt is passed through the frame of the buckle, at least a portion of the prong of the buckle is able to be moved relative to the frame of the buckle, between a first position where the prong extends through a hole in the first row of holes and rests against the anchor bar of the frame, and a second position where the prong extends through a hole in the second row of holes and rests against the anchor bar of the frame,
wherein the holes in the first row of holes are staggered relative to the holes in the second row of holes, and
wherein the first and second rows of holes are centered and symmetrical on the strap between a top side of the strap and bottom side of the strap,
the method comprising:
wrapping the belt around a person's waist;
passing the first end of the strap through the frame of the buckle;
tightening the belt to a desired tightness;
selecting a first hole for the prong between the first row of holes and the second row of holes;
pivoting the prong laterally, or sliding the prong along an end bar to align with the first selected hole; and
passing the prong through the first selected hole to rest against an anchor bar of the frame of the buckle.

12. The method of claim 11, further comprising:
pulling at the strap to disengage the prong from the selected hole;
loosening or tightening the belt as desired;
selecting a second hole for the prong, wherein the second hole is in a different one of the rows than the first selected hole;
pivoting the prong laterally, or sliding the prong along the end bar to align with the second selected hole; and
passing the prong through the second selected hole to rest against the anchor bar of the frame of the buckle.

13. The method of claim 11, wherein the belt is a weight lifting belt, the strap has a thickness between 3 millimeters and 15 millimeters, and at least a portion of the strap has a width that is between 30 millimeters and 125 millimeters.

14. The belt of claim 1, wherein the strap has a length between 500 millimeters and 1300 millimeters.

15. The belt of claim 1, wherein the first row of holes and the second row of holes are the only rows of holes in the strap of the belt.

16. The belt of claim 1, wherein a distance between adjacent holes in each respective one of the first and second rows of holes is no less than 1 inch.

17. A weightlifting belt comprising:
a strap having a first end and a second end opposite the first end,
wherein the strap has a thickness between 3 millimeters and 15 millimeters, at least a portion of the strap has a width that is between 30 millimeters and 125, and the strap has a length between 500 millimeters and 1300 millimeters,
a first row of holes that extends in a longitudinal direction near the first end of the strap;
a second row of holes that extends in the longitudinal direction near the first end of the strap,
wherein the first row of holes is parallel to the second row,
wherein the holes in the first row of holes are offset in the longitudinal direction from the holes in the second row of holes,
wherein the first row of holes and the second row of holes are the only rows of holes in the strap of the belt,
wherein the first and second rows of holes are centered and symmetrical on the strap between a top side of the strap and bottom side of the strap,
wherein a distance between adjacent holes in each respective one of the first and second rows of holes is no less than 1 inch; and
a buckle coupled to the second end of the strap,
wherein the buckle comprises a frame and one and only one prong,
wherein the frame comprises an end bar, to which the one and only one prong is physically coupled, and an anchor bar, against which the one and only one prong is able to rest,
wherein the buckle is configured such that when the first end of the belt is passed through the frame of the buckle, at least a portion of the one and only one prong of the buckle is able to be moved relative to the frame of the buckle, between a first position where the one and only one prong extends through a hole in the first row of holes and rests against the anchor bar of the frame, and a second position where the one and only one prong extends through a hole in the second row of holes and rests against the anchor bar of the frame.

18. A belt comprising:
a strap having a first end and a second end opposite the first end;
a first row of holes that extends in a longitudinal direction near the first end of the strap;
a second row of holes that extends in the longitudinal direction near the first end of the strap,
wherein the second row is parallel to the first row,
wherein the holes in the first row are offset in the longitudinal direction from the holes in the second row; and
a buckle coupled to the second end of the strap,
wherein the buckle comprises a frame and a prong,
wherein the frame comprises an end bar, to which the prong is physically coupled, and an anchor bar, against which the prong is able to rest,
wherein the buckle is configured such that when the first end of the belt is passed through the frame of the buckle, at least a portion of the prong of the buckle is able to be moved relative to the frame of the buckle, between a first position where the prong extends through a hole in the first row of holes and rests against the anchor bar of the frame, and a second position where the prong extends through a hole in the second row of holes and rests against the anchor bar of the frame,
wherein the holes in the first row of holes are staggered relative to the holes in the second row of holes, and
wherein the first row of holes and the second row of holes are the only rows of holes in the strap of the belt.

19. A method of wearing a belt, wherein the belt comprises:
a strap having a first end and a second end opposite the first end;
a first row of holes that extends in a longitudinal direction near the first end of the strap;
a second row of holes that extends in the longitudinal direction near the first end of the strap,
wherein the second row is parallel to the first row,
wherein the holes in the first row are offset in the longitudinal direction from the holes in the second row;
a buckle coupled to the second end of the strap,
wherein the buckle comprises a frame and a prong,
wherein the frame comprises an end bar, to which the prong is physically coupled, and an anchor bar, against which the prong is able to rest,
wherein the buckle is configured such that when the first end of the belt is passed through the frame of the buckle, at least a portion of the prong of the buckle is able to be moved relative to the frame of the buckle, between a first position where the prong extends through a hole in the first row of holes and rests against the anchor bar of the frame, and a second position where the prong extends through a hole in the second row of holes and rests against the anchor bar of the frame,
wherein the holes in the first row of holes are staggered relative to the holes in the second row of holes, and
wherein the first row of holes and the second row of holes are the only rows of holes in the strap of the belt,
the method comprising:
wrapping the belt around a person's waist;
passing the first end of the strap through the frame of the buckle;
tightening the belt to a desired tightness;
selecting a first hole for the prong between the first row of holes and the second row of holes;
pivoting the prong laterally, or sliding the prong along an end bar to align with the first selected hole; and
passing the prong through the first selected hole to rest against an anchor bar of the frame of the buckle.

\* \* \* \* \*